United States Patent [19] [11] 4,246,346
Larsson et al. [45] Jan. 20, 1981

[54] ANTIBIOTIC AND STEROID TRANSFORMATION PROCESS

[75] Inventors: Per-Olof Larsson, Lund; Klaus H. Mosbach, Furulunds Station; Sten A. Ohlson, Lund, all of Sweden

[73] Assignee: Aktiebolaget Fermenta, Strangnäs, Sweden

[21] Appl. No.: 939,117

[22] Filed: Sep. 5, 1978

Related U.S. Application Data

[63] Continuation of Ser. No. 812,996, Jul. 5, 1977, abandoned.

[51] Int. Cl.³ .............................................. C12P 33/14
[52] U.S. Cl. ......................................... 435/57; 435/44; 435/55; 435/58; 435/59; 435/60; 435/61; 435/244; 435/182
[58] Field of Search ...................... 195/59, 51 E, 51 S, 195/51 A, 51 C, 36 P, 80 R; 435/244, 44, 54, 55, 57, 58, 59, 60, 61

[56] References Cited

U.S. PATENT DOCUMENTS

| | | | |
|---|---|---|---|
| 2,538,721 | 1/1951 | Colingsworth | 195/36 P |
| 3,860,490 | 1/1975 | Guttag | 195/59 |
| 3,953,291 | 4/1976 | Chibata et al. | 195/36 P |
| 3,957,580 | 5/1976 | Nelson | 195/59 |
| 3,972,776 | 8/1976 | Vieth et al. | 195/59 |

OTHER PUBLICATIONS

Biotechnology and Bioengineering vol. XIII, pp. 503-515, (1971).
J. Gen. Appl. Microbiol. vol. 7, No. 2, 1961, pp. 113-117.
Applied Microbiology vol. 27, pp. 878-885, (1974).

*Primary Examiner*—Alvin E. Tanenholtz
*Attorney, Agent, or Firm*—Brumbaugh, Graves, Donohue & Raymond

[57] ABSTRACT

A method for activating immobilized living microorganisms applied to transformations of steroids, antibiotics and other compounds characterized by the addition of peptone, glucose or a mixture of peptone and glucose to the reaction mixture.

7 Claims, No Drawings

ANTIBIOTIC AND STEROID TRANSFORMATION PROCESS

This is a continuation of application Ser. No. 812,996 filed July 5, 1977 and now abandoned.

This invention relates to a method of activating immobilized microorganisms. Particularly this invention relates to a method for activating immobilized living microorganisms applied to transformations of steroids, antibiotics and other compounds.

PRIOR ART

Immobilized microorganisms having attracted an increasing interest as catalysts in the last few years (Biotechnol. Bioeng. 17, 1797–1804 (1975); J. Appl. Chem. Biotechnol. 25, 115–141 (1975); Biotechnol. Bioeng. 12, 19–27 (1970). They exhibit the same operational advantages as those inherent in immobilized enzymes (FEBS Lett. 62. (supplement) E 80–E 90 (1976)); they are reusable, they are well suited for continuous operation under controlled conditions and further they are comparatively resistant to microbial attack, since they are protected by the polymer. Immobilized microorganisms offer the additional advantage that tedious and costly enzyme isolation is obviated, that the enzyme is more usually stable due to its localization in its "natural environment", and that there is usually no cofactor requirement. Thus, provided competing reactions can be eliminated, immobilized microorganisms are very promising catalysts. However, in continuous or repeated batch operation of the transformation process the activity declines rather rapidly when immobilized microorganisms are used. This problem has hitherto not been satisfactorily solved in connection with immobilized living microorganisms.

AREAS OF APPLICATION

In the present application there is especially considered a property unique to immobilized living whole-cell catalysts, namely the possibility of in situ activation of the immobilized enzymic activity.

Suitable substrates for transformations wherein the activation according to the invention can be applied are
  (1) steroids, particularly corticosteroids, for instance cortisol
  (2) antibiotics, such as penicillin G
  (3) other compounds such as
      a. alkaloids, e.g. solasodine, tomatidine
      b. organic acids, e.g. N-acetyl-L-amino acids
      c. carbohydrates, e.g. glucose, sorbose
      d. purin bases, nucleosides and nucleotides, e.g. 6-chloropurine, 6-chloropurine riboside The activation can be applied to several systems, such as the corticosteroid transformation cortisol $\Delta^1$-dehydrogenase prednisolone. The reaction can be catalyzed by polyacrylamide entrapped Corynebacterium simplex (Arthrobacter simplex).

Among transformations suitable for the activation according to the invention could be mentioned
  (1) $\Delta^1$-dehydrogenation. Incorporation of a double bond in the 1,2-position of the steroid molecule. Example:
$\Delta^1$-dehydrogenation of Cortisol and derivatives of Cortisol e.g. Cortisol to Prednisolon,
9α-Fluor-16β-methylcortisol to 9α-Fluor-16β-methylprednisolon (Betametason),
9α-Fluor-16α-methylcortisol to 9α-Fluor-16α-methylprednisolon (Dexametason),
6α-methylcortisol to 6α-Methylprednisolon,
6α-Fluor-16α-methylcortisol to 6α-Fluor-16α-methylprednisolon (Parametason),
9α-Fluor-16α-hydroxicortisol to 9α-Fluor-16α-hydroxipradnisolon (Triamcinolon),
9α-Fluorcortisol to 9α-Fluorprednisolon,
6α, 9α-Difluor-16α, 17α-isopropylidendioxicortisol to 6α, 9α-Difluor-16α, 17α-isopropylidendioxiprednisolon (2) 11 α-hydroxylation. Incorporation of a hydroxy group in the 11α-position of the steroid molecule. Example: transformation of cortexolone and derivatives of cortexolone to 11α-hydroxy cortexolone (epicortisol) and derivatives of epicortisol.

(3) 11β-hydroxylation. Incorporation of a hydroxy group in the 11β-position of the steroid molecule. Example: 11β-Hydroxylation of Cortexolon and derivatives of Cortexolon e.g. Cortexolon to Cortisol,
9α-Fluor-16β-methylcortexolon to 9α-Fluor-16β-methylcortisol,
9α-Fluor-16α-methylcortexolon to 9α-Fluor-16α-methylcortisol,
9α-Fluorocortexolon to 9α-Fluorcortisol,
6α-Fluor-16α-methylcortexolon to 6α-Fluor-16α-methylcortisol,
6α-Methylcortexolon to 6α-methylcortisol,
6α, 9α-Difluorcortexolon to 6α, 9α-Difluorcortisol,
6α, 9α-Difluor-16α, 17α-isopropylidendioxicortexolon to
6α, 9α-Difluor-16α, 17α-isopropylidendioxicortisol.

(4) 16α-hydroxylation. Incorporation of a hydroxy group in the 16α-position of the steroid molecule. Example:
16α-Hydroxylation of Cortisol and derivatives of Cortisol, e.g. Cortisol to 16α-Hydroxicortisol,
6α-Fluorcortisol to 6α-Fluor-16α-hydroxicortisol,
9α-Fluorcortisol to 9α-Fluor-16α-hydroxicortisol,
6α, 9α-Difluorcortisol to 6α, 9α-Difluor-16α-hydroxicortisol.

(5) Penicillin G transformation. Transformation of benzylpenicillin (penicillin G) to 6-aminopenicillanic acid, (6) Side-chain elimination. Example: transformation of sitosterol to $\Delta^4$-androstene-3,17-dione. cholesterol to $\Delta^{1,4}$-androstadiene-3,17-dione, (7) 12α-hydroxy elimination. Example: transformation of cholic acid to chenodesoxycholic acid.

Suitable organisms which can be used in connection with this invention are (1) *Arthrobacter simplex* (also called *Corynebacterium simplex*, for instance ATCC 6946). This organism can be used for $\Delta^1$-dehydrogenation.

(2) *Rhizopus nigricans* (also called *Rhizopus stolinifer*, for instance ATCC 6227 b). This organism can be used for 11 α-hydroxylation.

(3) *Curvularia lunata*, for instance ATCC 12017. This organism can be used for 11 β-hydroxylation.

(4) *Escherichia coli*, for instance ATCC 9637. This organism can be used for 6-aminopenicillanic acid production from penicillin G.

(5) *Aspergillus niger*. This organism can be used for 16α-hydroxylation.

(6) *Streptomyces venezuelae*. This organism can be used for isomerization of glucose.

(7) *Brevibacterium ammoniogenes*. This organism can be used for transformation of purin bases, nucleosides and nucleotides.

The microorganisms are immobilized in a suitable carrier, such as polyacrylamide, agar (2.5–15% w/v), collagen (cell:collagen 1:1) or calcium alginate (1–5%).

OUTLINE OF THE INVENTION

This invention provides a method to prevent the decline of activity of immobilized living microorganisms and even to enhance the activity at repeated or continuous operation. More particularly this invention provides a method for activating immobilized living microorganisms applied to transformations of steroids, antibiotics and other compounds where immobilized microorganisms are used, characterized by the addition of peptone and glucose to the reaction mixture. Preferably peptone should be used in the concentration range of 0.1–1.0 (w/v). 0.1% (w/v) peptone and 0.2% (w/v) glucose in combination gives also good results. The temperature at the process should be 20°–30° C. and the process should be conducted at aerobic conditions.

EXPERIMENTAL

Example 1

In this experiment the system studied was the important corticosteroid transformation cortisol $\Delta^1$-dehydrogenase prednisolone. The reaction was catalyzed by polyacrylamide-entrapped Arthrobacter simplex, (also called Corynebacterium simplex).

A. simplex cells were grown in a medium of 0.25% yeast extract; the $\Delta^1$-dehydrogenase activity being induced by addition of cortisol to the culture 12 hours prior to harvesting by continuous centrifugation at 10.000×g. The cells (5 g wet weight) were suspended in 20 ml of ice-cold 0.1 M Tris-HCl buffer, pH 7.5 and mixed with 25 ml ice-cold aqueous monomer solution containing 7.13 g acrylamide and 0.38 g N,N$^1$-methylene-bis-acrylamide. The mixture was poured into a sandwich-like polymerization vessel (made of two glass plates 20×20×0.2 cm, spaced 2 mm apart with a piece of latex tubing) and the catalysts potassium persulphate (50 mg) and tetramethylethylenediamine (100 mg) were added in water (1 ml). Nitrogen gas was bubbled through the suspension and the polymerization started within 2 minutes. The polyacrylamide gel sheet was fragmented in a blender and the gel granules (average size 0.2 mm) were washed extensively with Tris buffer and then stored at $-20°$ C., at which temperature the preparation was stable for several months.

The 3-ketosteroid-$\Delta^1$-dehydrogenase activity of the immobilized A. simplex was conveniently assayed by a spectrophotometric procedure and the sole product, prednisolone, was identified by thin-layer chromatography. Approximately 40% of the dehydrogenase activity was retained during the immobilization procedure (all bacteria added were immobilized and no release of bacteria was observed during incubations). Initial experiments revealed, however, that the activity declined rather rapidly on repeated batchwise conversions of high loads of cortisol and this could only be compensated for to a limited degree by addition of the artificial electron acceptor menadione. Instead the stabilizing influence of various nutrients and salts was investigated; the results are given in the Tables I and II. In media consisting of water or buffer the activity decreased, whereas in peptone- and glucose-containing media the activity was not only preserved but also dramatically increased to several times that of the original activity. The 0.5% peptone medium and the 0.1% peptone+0.2% glucose medium were selected for further study and an experiment with repeated batch-wise transformation was conducted. Both media were approximately equally efficient and in Table III the results obtained with the 0.5% peptone medium are depicted. As can be seen, the transformation capacity increased remarkably with each run, thus while in the first batch 100% transformation was obtained after 18 hours, the last batch was completed in less than 2 hours. The transformation capacity at the end of the experiment was approximately 0.5 g steroid/day/g gel (wet weight).

Example 2

Recent preliminary experiments show that the so-called pseudocrystallofermentation technique is applicable also to entrapped A. simplex. Cortisol was thus added in an amount (3.6 g/l) by far exceeding its solubility in the medium and was completely converted at approximately the same rate as in experiments with dissolved cortisol. The product prednisolone, which precipitated out, could be isolated simply by filtration after the rather dense gel granules had been allowed to settle. This technique allows reduction of media volumes by orders of magnitude and thus also of nutrients.

TABLE I

Activating effect of nutrients, buffers and salts on 3-ketosteroid-$\Delta^1$-dehydrogenase activity of immobilized A.simplex

| Medium[a] | Initial transformation rate[b](%) after | | | | |
|---|---|---|---|---|---|
| | 0 | 2 | 6 | 10 | 16 days |
| Peptone 0.5% | 100 | 460 | 500 | 650 | 530 |
| Glucose 0.2% | 100 | 210 | 170 | 110 | 90 |
| K$_2$HPO$_4$, 0.1M, pH 7.0 | 100 | 70 | 50 | 60 | 60 |
| Tris-HCl, 0.05M, pH 7.0 | 100 | 100 | 70 | 70 | 30 |
| K$_2$HPO$_4$, 0.1M, pH 7.0 / ZnCl$_2$, FeCl$_2$ | 100 | 50 | 25 | 15 | 10 |
| K$_2$HPO$_4$, 0.1M, pH 7.0 / CoCl$_2$, MgSO$_4$ | 100 | 40 | 40 | 0 | 0 |
| K$_2$HPO$_4$, 0.1M, pH 7.0 / MgCl$_2$, CaCl$_2$ | 100 | 160 | 130 | 80 | 90 |
| K$_2$HPO$_4$, 0.1M, pH 7.0 / Peptone 0.5% / Glucose 0.2% / MgCl$_2$, CaCl$_2$ | 100 | 560 | 650 | 600 | 550 |
| H$_2$O | 100 | 60 | 40 | 40 | 20 |

[a] the concentration of the inorganic salts MgCl$_2$, ZnCl$_2$, CoCl$_2$, FeCl$_2$, CaCl$_2$ and MnSO$_4$ was 1mM.
[b] activity of freshly prepared gel is set to 100%

A. simplex gel (0,5 g) was incubated in 9.0 ml of medium as indicated and 0,5 ml 20 mM cortisol (methanol) was added. The suspension was shaken on a rotary shaker at 25° C. and at 48 h intervals the medium was replaced by fresh cortisol-containing medium. At the intervals indicated the gel was filtered off, washed and assayed for $\Delta^1$-dehydrogenase activity.

TABLE II

Activating effect of peptone/glucose on 3-ketosteroid-$\Delta^1$-dehydrogenase activity of immobilized A.simplex[a]

| Medium | Initial transformation rate[b] (%) after | | | | |
|---|---|---|---|---|---|
| | 0 | 2 | 6 | 10 | 16 days |
| Peptone 1% | 100 | 290 | 320 | 380 | 550 |
| 0.5% | 100 | 460 | 500 | 650 | 530 |
| 0.1% | 100 | 200 | 225 | 165 | 120 |
| 0.01% | 100 | 125 | 30 | 0 | 0 |
| Peptone 0.1% | 100 | 250 | 225 | 240 | 350 |

TABLE II-continued

Activating effect of peptone/glucose on 3-ketosteroid-$\Delta^1$-dehydrogenase activity of immobilized A.simplex[a]

| Medium | Initial transformation rate[b] (%) after | | | | |
|---|---|---|---|---|---|
| | 0 | 2 | 6 | 10 | 16 days |
| Glucose 0.2% Peptone 0.01% | 100 | 110 | 55 | 0 | 0 |
| Glucose 0.2% | | | | | |
| Glucose 0.2% | 100 | 210 | 170 | 110 | 90 |

[a] experimental conditions are given in table I.
[b] activity of freshly prepared gel is set to 100%

TABLE III

Repeated batch-wise transformation of cortisol to prednisolone

| Run (no) | Transformation capacity (mg prednisolone/hour /g gel (wet weight)) | Time for 100% conversion (h) |
|---|---|---|
| 1 | 3.1 | 17.4 |
| 2 | 5.0 | 10.8 |
| 3 | 13.5 | 4.0 |
| 4 | 18.1 | 3.0 |
| 5 | 26.3 | 2.1 |
| 6 | 27.1 | 2.0 |
| 7 | 27.1 | 2.0 |
| 8 | 29.6 | 1.8 |
| 9 | 30.8 | 1.8 |
| 10 | 31.7 | 1.7 |

*A. simplex* gel (2.0 g) was suspended in 285 ml of 0.5% peptone, pH 7.0 + 15 ml of 20 mM cortisol (methanol). The progress of the transformation was followed spectrophotometrically and when 100% conversion to prednisolone was reached the gel was washed and again incubated with fresh cortisol-containing medium. The whole experiment lasted 4 days.

We claim:

1. In antibiotic and steroid transformation processes, wherein an immobilized living microorganism is used as a catalyst to transform a substrate which is an antibiotic or a steroid, the method of activating said catalyst comprising adding to a reaction mixture containing said catalyst and substrate to be transformed thereby, peptone or a mixture of peptone and glucose.

2. The method according to claim 1 wherein said substrate is cortisol or a cortisol derivative selected from the group consisting of 6 alpha-, 9 alpha-difluoro derivative, 6 alpha fluoro-, 16 alpha-methyl derivative, 9 alpha fluoro-, 16 alpha-hydroxy derivative, and 6 alpha, 9 alpha difluoro 16 alpha-, 17 alpha-isopropylidenedioxy derivative, and is delta 1-dehydrogenated to the corresponding prednisolone compound in said reaction mixture.

3. The method according to claim 1 wherein said substrate is a steroid which is transformed by a 11- or 16-hydroxylation thereof.

4. The method according to claim 1 wherein said catalyst is a microorganism transforming the steroid by dehydrogenation transformation thereof.

5. The method according to claim 1 wherein a steroid transformation is catalyzed by *Arthrobacter simplex*.

6. The method according to claim 1 wherein the catalyst is a microorganism entrapped in polyacrylamide gel.

7. The method according to claim 1, wherein the amount of peptone or a mixture of peptone and glucose added to the reaction mixture is between 0.1–1.0% (weight/volume).

* * * * *

UNITED STATES PATENT AND TRADEMARK OFFICE
CERTIFICATE OF CORRECTION

PATENT NO. : 4,246,346
DATED : January 20, 1981
INVENTOR(S) : Per Olof Larsson, et al.

It is certified that error appears in the above—identified patent and that said Letters Patent is hereby corrected as shown below:

On the Title page, item [22] of patent after "Appl. No.: 939,117" insert --Priority Claim of Swedish Appln. No. 7607698-3 filed July 6, 1976--;

Col. 1, line 14, "having" should read --have--;

Col. 1, lines 56-57, " $\Delta'$-dehydrogenase" should read -- $\underline{\Delta'\text{-dehydrogenase}}$--;

Col. 2, line 7, "ipradnisolon" should read --iprednisolon--;

Col. 2, lines 66-68, "This organism ...nucleotides." should not appear in italics;

Col. 3, lines 24-25, " $\Delta'$-dehydrogenase" should read -- $\underline{\Delta'\text{-dehydrogenase}}$--.

Signed and Sealed this

Seventeenth Day of August, 1993

Attest:

BRUCE LEHMAN

Attesting Officer

Commissioner of Patents and Trademarks